United States Patent [19]

Braquet

[11] Patent Number: 4,734,280

[45] Date of Patent: Mar. 29, 1988

[54] TREATMENT OR PREVENTION OF PAF ACETHER-INDUCED MALADIES

[75] Inventor: Pierre Braquet, Garches, France

[73] Assignee: Societe de Conseils de Recherches et d'Applications Scientifiques (S.C.R.A.S.), France

[21] Appl. No.: 693,716

[22] Filed: Jan. 23, 1985

[30] Foreign Application Priority Data

Jul. 19, 1984 [GB] United Kingdom ............... 8418424

[51] Int. Cl.$^4$ ...................... A61K 35/78; A61K 31/34
[52] U.S. Cl. ................................. 424/195.1; 514/470; 514/920
[58] Field of Search ..................... 424/195.1; 514/470, 514/920

[56] References Cited

PUBLICATIONS

Chem. Abst. 77: 152375d, 1972.
J. Benveniste et al., "The Actions of PAF-Acether (Platelet-Activating Factor) on Guinea-Pig Isolated Heart Preparations", Br. J. Pharmac., 80, pp. 81–83, 1983.
K. Nakanishi, "The Ginkgolides", Pure and Applied Chemistry, 14, pp. 89–113, 1967.
M. Maruyama et al., "The Ginkgolides, Derivation of Partial Structures", Tetrahedron Letters No. 4, pp. 303–308, 1967.
K. Okaha et al., "Ginkgolides", J. Chem. Soc. (C), No. 74, pp. 2201–2206, 1967.
R. Bourgain et al., "A Continuous Registration Method in Experimental Arterial Thrombosis in the Rat", Thrombosis Research, vol. 4, pp. 599–607, 1974.
G. Camussi et al., "Platelet Activating Factor-Mediated Contraction of Rabbit Lung Strips: Pharmacologic Modulation", Immunopharmacology 6, pp. 87–96, 1983.
G. Basran et al. "Cromoglycate (DSCG) Inhibits Responses to Platelet-Activating Factor (PAF-Acether) in Man: An Alternative Mode of Action for DSCG in Asthma?", European Journal of Pharmacology, 86, pp. 143–144, 1983.
M. Sanchez-Crespo et al., "Vascular Actions of Synthetic PAF-Acether in the Rat: Evidence for a Platelet Independent Mechanism", Immunopharmacology 4, pp. 173–185, 1982.
R. Vargaftig, et al. "Non-Steroidal Anti-Inflammatory Drugs if Combined with Anti-Histamine and Anti-Serotonin Agents Interfere with the Bronchial and Platelet Effects of PAF-Acether", European Journal of Pharmacology, 82, pp. 121–130, 1982.
M. Braquet et al., "Leucocyte Leukotriene B$_4$ Secretion Precedes Anergy in Burn-Injured Patients", The Lancet, No. 8409, Oct. 27, 1984, p. 976.
M. Braquet et al. "Leukocytic Functions in Burn-Injured Patients", Prostaglandins, 29, No. 5, p. 747, May 1985.

*Primary Examiner*—Johnnie R. Brown
*Assistant Examiner*—John W. Rollins
*Attorney, Agent, or Firm*—Lucas & Just

[57] ABSTRACT

The present invention relates to the treatment of PAF Acether-induced maladies. The treatment comprises the administration of a ginkgolide or a ginkgolide derivative. Ginkgolide B has been found to be the most effective. The ginkgolides may be introduced orally, intraveneously or by spray inhalation.

12 Claims, 5 Drawing Figures

FIG. 1

TREATMENT OR PREVENTION OF PAF ACETHER-INDUCED MALADIES

The present invention relates to the treatment or prevention of PAF Acether-induced maladies. The treatment comprises the administration of an effective amount of one or more ginkgolides or derivatives thereof, alone or in admixture with a pharmaceutically acceptable diluent or carrier.

PAF Acether (Platelet Activating Factor) is a known phospholipid which can cause maladies in animals, including humans. As reported by Benveniste et al., the PAF Acether causes aggregation of platelets and provokes the release of their vasoactive amines. As also reported by Benveniste, it also stimulates neutrophils to aggregate and release their proinflammatory content, see J. BENVENISTE, C. BOULLET, C. BRINK and C. LABAT, Brit. J. Pharmacol, The action of PAF Acether on guinea-pig isolated heart preparation, 80: 81-3 (1983).

It is commonly understood that a PAF Acether release is induced in animals, including humans, upon the happening of various kinds of shocks such as anaphylactic shocks, burns, septic shocks, irradiation shocks and traumae. There is a strong release of PAF-Acether in the hours following the shock, which leads thereafter to a suppression of immunitory reactions due to the exhaust of the defensive means of the organism. While many compounds have been tried for the treatment or prevention of PAF Acether-induced maladies, the rate of effectiveness has not been very great. These treatments are discussed more fully in the examples infra.

The applicant has now discovered that PAF Acether-induced maladies can be effectively treated by the administration of a ginkgolide or a ginkgolide derivative. The ginkgolides are in many cases surprisingly more effective in treatment of PAF Acether-induced maladies than the compounds which are presently used for the treatment of PAF Acether-induced maladies. Of equal or greater advantage is the highly selective nature of the ginkgolides. While they are highly effective against platelet aggregation caused by PAF Acether, they exhibit virtually no inhibition against platelet aggregation caused by other factors. In particular, they do not interfere with aggregations induced by ADP, thrombine, collagen, adrenaline, histamine, $LTB_4$-, and serotonin. The applicant's discovery of this highly selective nature of inhibition of PAF Acether-induced platelet aggregation by the ginkgolides is most important.

Ginkgolides have been known for many years. They have been found in Ginkgo Biloba extracts but, to date, no therapeutical activity has been found for this group of compounds. These compounds may be obtained as described by KOHI NAKANISHI, Pure and Applied Chemistry, 14 (1967) 89. Their structures are also described by MARUYAMA and Al., Tetrahedron Letters (1967) 299, 303.

The ginkgolides are derived from the gymnospermous tree Ginkgo Biloba. Commmonly available ginkgolides include Ginkgolide A, Ginkgolide B, Ginkgolide C, and Ginkgolide M. Each of these has been found to be effective in treating PAF Acether-induced maladies. Of these four, Ginkgolide B has been found to be the most effective.

Derivatives of the ginkgolides are also known. Common derivatives include the mono-acetate, the tri-acetate, the tetrahydro and the acetyl, see K. OKABE, K. YAMADA, S. YAMAMURA, and S. TAKADA, Ginkgolides, J. Chem. Soc. (C), 1967, 2201-2206.

In the treatment of PAF Acether-induced maladies, the ginkgolides can suitably be administered orally, intravenously (including by perfusion), or by spray inhalation at doses from 1 to 50 mg/kg. In addition to use in the treatment of PAF Acether-induced maladies, the ginkgolides can also be used to prevent the onset of PAF Acether platelet aggregation in high risk situations.

The antagonist action of Ginkgolides administration against the platelets aggregation incuded by PAF-Acether brings a correlative shortening of the post-trauma period during which the immunitory means of the organism are lowered or suppressed.

These and other advantages of the present invention may be more fully understood by the discussion which follows concerning the effectiveness of the compounds in treatment of PAF Acether-induced maladies as compared to literature-reported compounds for the same treatment.

I Binding Determinations

The competition of the alternative binding of either $^3$H-PAF Acether or one of the Ginkgolides was evidenced by radioactive determinations using a rabbit membrane platelet preparation. (100% control=$^3$H-PAF Acether alone). At $10^{-4}$M, Ginkgolide M reduced the binding by 79%. At $10^{-5}$M, Ginkgolides A and C reduced the binding respectively by 67 and 83%. At $10^{-6}$M, Ginkgolide B reduced the binding by 94%.

$IC_{50}$ determined in these conditions for Ginkgolide B was equal to $5.75 \cdot 10^{-7}$M.

For testing the specificity of action of these compounds, on PAF-Acether receptor the binding of the Ginkgolides was also checked on other types of receptors: $H_1$, $H_2$, 5-HT, $5HT_2$, $\alpha_1$, $\alpha_2$, $\beta_1$, $\beta_2$, etc . . . : no noticeable binding was seen, demonstrating their specificity of action.

II Inhibition of Platelets Aggregation (PA)

1-Rabbit PA 1.1. In vitro study:

The Inhibition of PAF Acether-induced PA has been studied on rabbit plasma-rich platelets (PRP). Two doses of PAF Acether were used (2.5 nM and 5 nM). The tested compound was added to the medium 3 minutes before PAF Acether and aggregation was followed by monitoring changes in electrical impedance (Whole-Blood aggregometer-chrono-Log); kadsurenone was simultaneously tested as reference compound and the $IC_{50}$ molar doses of Ginkgolides A, B, C and M and of kadsurenone on PAF Acether-induced rabbit PA (PRP) have been calculated.

Figure 1:
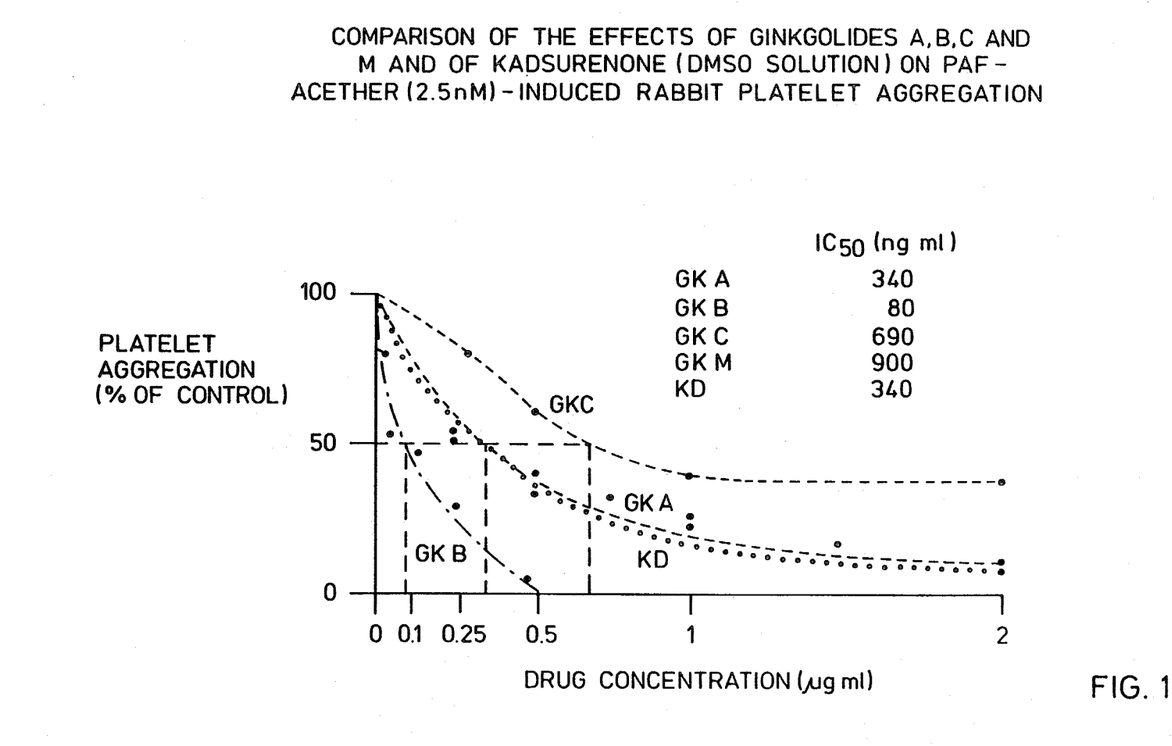

The results obtained are presented in the following table (average values for 10 assays for each dose) and FIG. 1:

| $IC_{50}$ doses of (M) | For PAF Acether doses (in nM) | |
|---|---|---|
| | 2.5 | 5 |
| Ginkgolide A | $8.32 \cdot 10^{-6}$ | $1.32 \cdot 10^{-5}$ |
| Ginkgolide B | $1.88 \cdot 10^{-6}$ | $3.20 \cdot 10^{-6}$ |
| Ginkgolide C | $1.53 \cdot 10^{-5}$ | $2.54 \cdot 10^{-5}$ |
| Ginkgolide M | $1.22 \cdot 10^{-4}$ | $2.02 \cdot 10^{-5}$ |
| Kadsurenone | $9.94 \cdot 10^{-6}$ | $1.40 \cdot 10^{-5}$ |

Ginkgolides A, B, C and M were totally ineffective against aggregation induced by other known aggregants such as: ADP, thrombine, calcium ionophore A 23187, collagen and adrenaline.

This result shows the high specificity of action of Ginkgolides.

Figure 2:
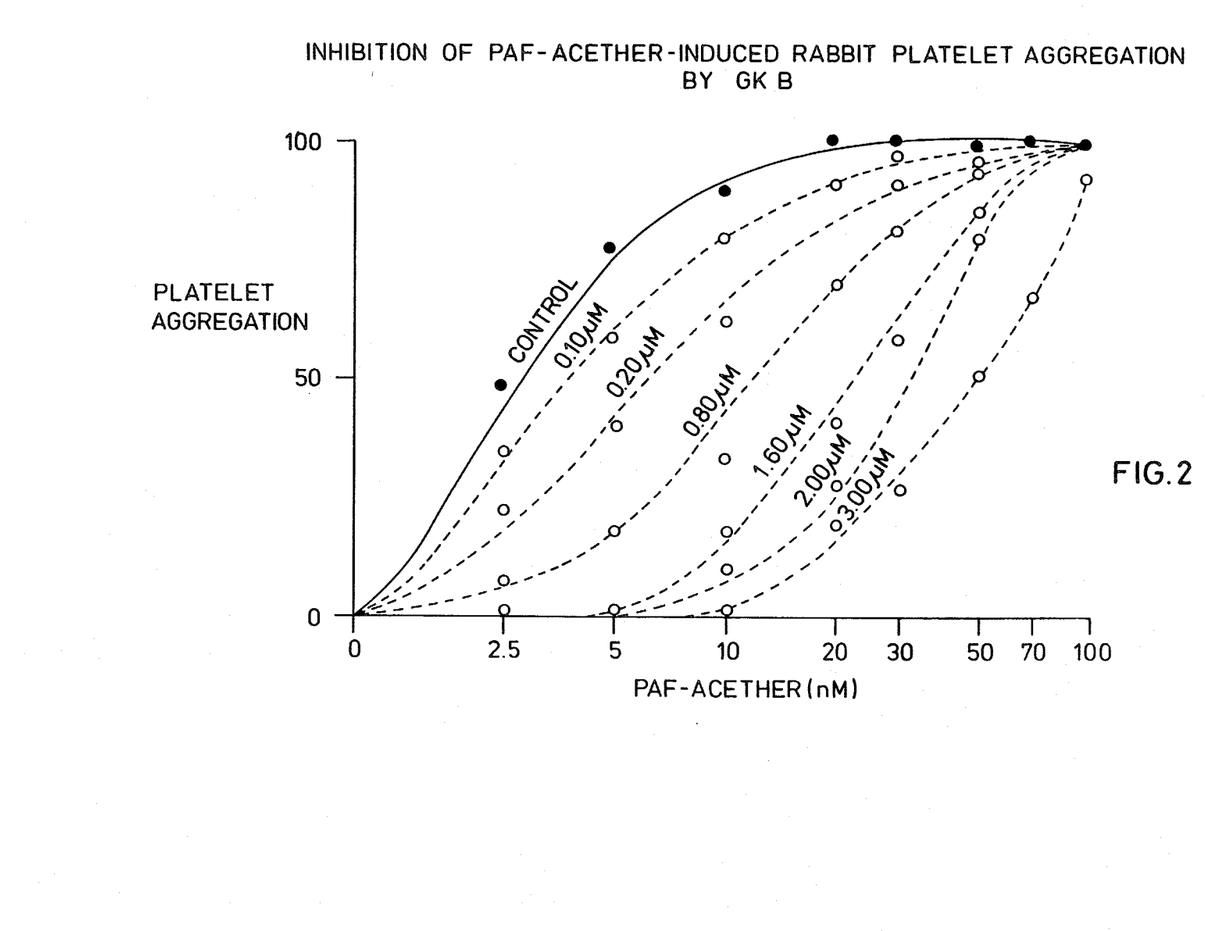

FIG. 2 present the dose/activity relationship obtained with Ginkgolide B.

1.2. Ex vivo study:

Drugs were administered per os (2,5 and 10 mg/kg) or by IV route (0.5, 1, 2 mg/kg) and blood samples were taken at different times to test platelet aggregation with PAF-Acether (2.5 and 5 nm) (see following table wherein the figures appearing are the ratio to the control with the solvent used, i.e. DMSO).

INHIBITION OF PAF ACETHER-INDUCED RABBIT PA BY GINKGOLIDE B ( % of control)(*)

| Administration | PAF Acether | | | | | |
|---|---|---|---|---|---|---|
| Mode | 2.5 nM | | | 5.0 nM | | |
| (mg/kg) | 0.5 h | 1 h | 2 h | 0.5 h | 1 h | 2 h |
| PER OS | | | | | | |
| 2 | 23 | 37 | 54 | 34.5 | 47.8 | 71.2 |
| 5 | 0 | 7 | 10 | 6 | 11.4 | 27.1 |
| 10 | 0 | 0 | 0 | 0 | 0 | 0 |
| IV | | | | | | |
| 0.5 | 0 | 7.4 | 11.2 | 0 | 9.4 | 14.5 |
| 1 | 0 | 0 | 4.1 | 0 | 1.1 | 7.2 |
| 2 | 0 | 0 | 0 | 0 | 0 | 0 |

(*) average values for one batch of 5 assays.

2-Human PA

2.1. In vitro study
2.1.1. PRP

The inhibition of PAF Acether-induced PA has been studied on human PRP. The same protocol was used as for rabbit hereinabove.

| IC Doses (M) of | PAF Acether Dose (nM) 100 |
|---|---|
| Ginkgolide A | $9 \cdot 10^{-5}$ |
| Ginkgolide B | $5.6 \cdot 10^{-5}$ |
| Ginkgolide C | $1.5 \cdot 10^{-4}$ |
| Kadsurenone | $1.3 \cdot 10^{-4}$ |

All ginkgolides were more effective than kadsurenone.

Figure 3:
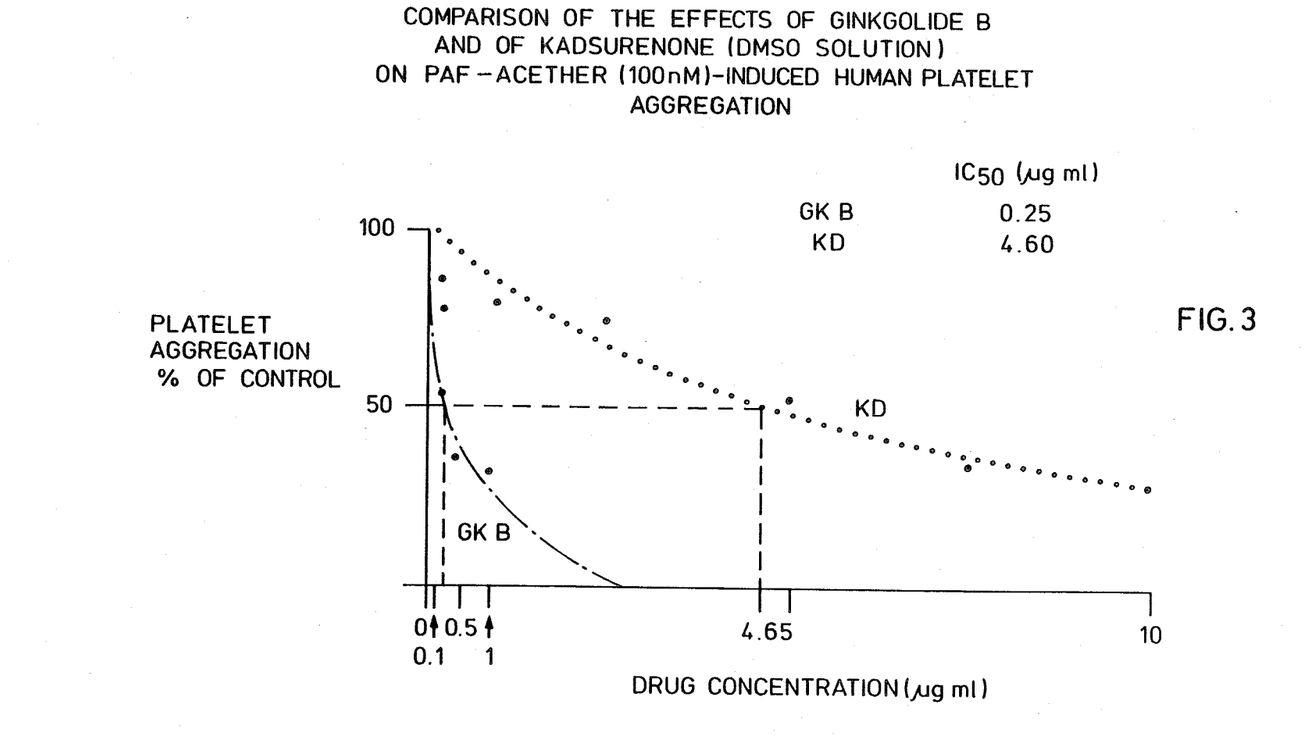

FIG. 3 shows the comparison of the inhibition obtained with the most potent Ginkgolide (GK B) and the reference product (kadsurenone).

2.1.2. Washed Platelets

The inhibition of PAF Acether-induced PA was also experimented using human washed platelets on Ginkgolides A, B, and C.

Best figure for $IC_{50}$ was obtained with Ginkgolide B (GK B) (average values of 5 assays) with $2.5 \cdot 10^{-5}$M.

Figure 4:
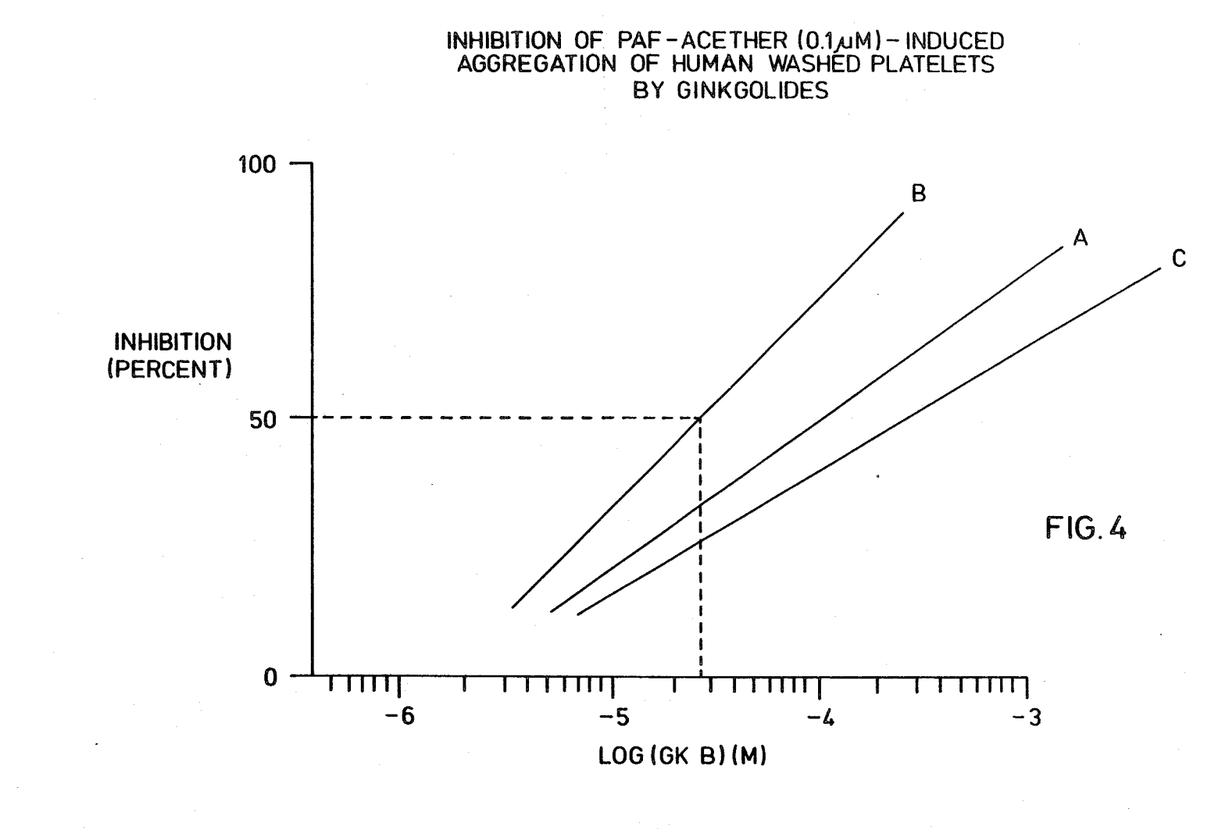

FIG. 4 shows the dose/activity relationship.

2.2. Ex vivo study (Ginkgolides A, B and C)

The same protocol described hereinabove for rabbit was used in man with only one dose of each Ginkgolide (IV 25 mg) and two blood takes (at 0.5 h and 1 h). Results are given in the following table:

| Time before blood take (hours) | PAF Acether (100 nM) | |
|---|---|---|
| | 0.5 | 1.0 |
| % of aggregation with | GK A 0 | 5.7 |
| respect to control | GK B 0 | 3.4 |
| | GK C 0 | 10.6 |

3-Opto electronic follow-up of platelet wessel wall interaction

In this experimental study, 20 guinea-pigs were used. The technical details concerning the operative procedure, the induction of focal deendothelialization, and the methodology of the electronically controlled microprojection procedures have been previously described in detail (Bourgain, R., and Six, F. (1974): a continuous registration method in experimental arterial thrombosis in the rat. Thromb. Reg. 4: 599–607). Briefly summarized, this method consists in the dissection over a distance of 2 to 3 mm of a branch of the mesenteric artery following gently extraction of a loop of small intestine. By transillumination, the image of this arterial segment is projected onto a set of 30 light-depending resistances (LDR) arranged in two columns of 15 elements each. An LDR element has the property to change its internal resistance as a function of a variation of light intensity. Each LDR is connected into its own Wheatstone bridge, and the changes in light intensity due to thrombus formation will be recorded as variations in electrical potentials and registered as such via a multiplexing device.

In the present investigation, several discriminating parameters are recorded: (a) the $t_1$ interval or the lag period (this is the time interval between the beginning of the PAF Acether superfusion and the first signs of thrombus formation; (b) the $t_d$ interval is the duration of the thrombotic phenomenon; (c) the O(t) curve indicates the number of LDR elements covered by the thrombus image; (d) the D(t) curve represents during each $30 \times 1/9 \times 10^{-2}$ sec interval the greatest potential deviation on one of the LDR elements covered by the thrombus image; (e) the T(t) curve represents the summation of the potentials registered on the LDR elements during a time interval of $30 \times 1/9 \times 10^{-2}$ sec the TTV(t) curve results from the integration of the T(t) values in function of time; (f) $m_D$, $m_T$, and $m_O$ correspond to the maximal values registered on, respectively, the D(t), T(t), and O(t) curves; (g) TTV is the maximal value of the TTV(t) curve, whereas TVM is the value of this curve up to the point where $m_T$ is reached.

In a first series of experiments (10 animals) the effect of local superfusion with PAF Acether ($10^{-4}$M) is investigated.

In a second series of experiments (10 animals) the effects of Ginkgolide B and of kadsurenone have been compared preventively and curatively.

PAF Acether superfusion induced a large and occlusive thrombus. Only prostacycline superfusion in the same time than PAF Acether superfusion might partially inhibit this phenomenon. Furthermore, to date, no drug was known to have a curative action against a pre-formed thrombus while Ginkgolide B or kadsurenone, when superfused with PAF Acether, no thrombus appeared demonstrating the efficiency of these agents.

Figure 5:
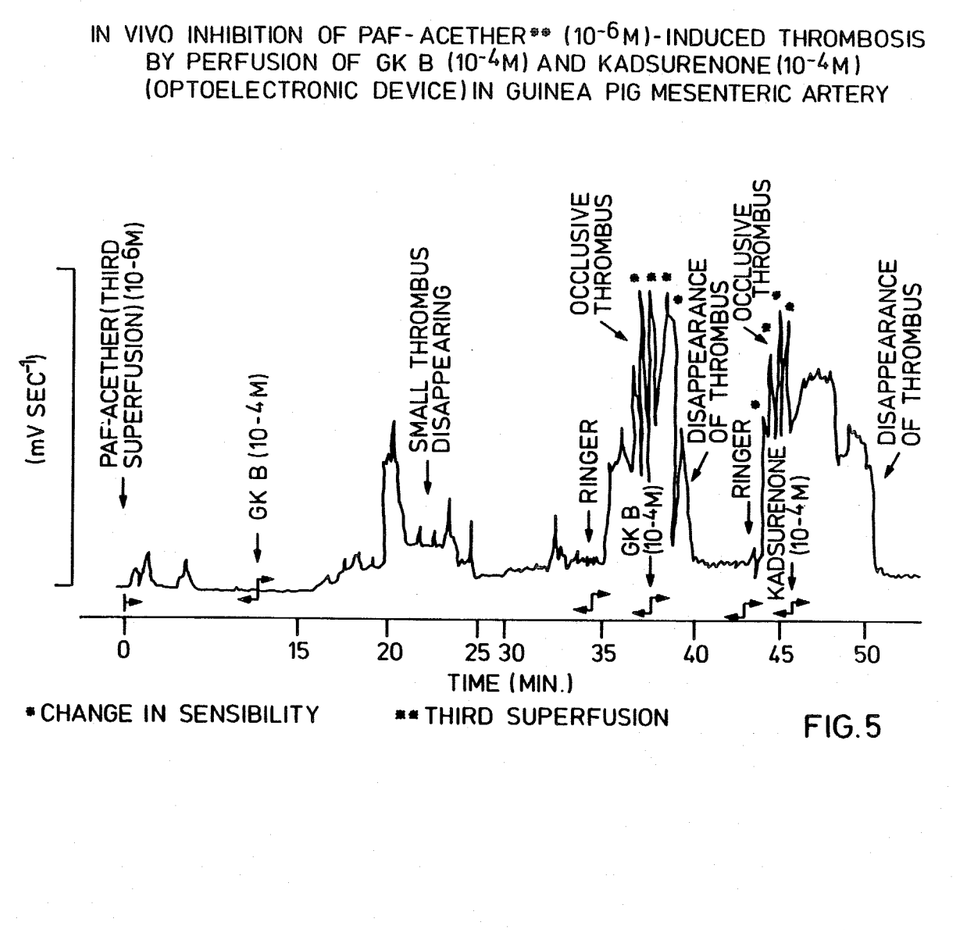

Surprisingly, as shown in the following figures, Ginkgolide B and kadsurenone were able to disaggregate such pre-formed thrombus but with a strong advantage for Ginkgolide if time is taken into consideration (about 4.30 minutes for disappearance of thrombus with kadsurenone against 2.30 minutes for Ginkgolide B).

FIG. 5 shows the results obtained after the third superfusion of PAF Acether in the guinea-pig mesenteric artery.

III Isolated organs

3.1. Contraction of superfused lung parenchymal strip induced by PAF Acether The antagonistic effect of preventive superfusion of 30 µg/ml of each of the Ginkgolides against PAF Acether (3 ng)-induced contraction of guinea-pig lung parenchymal strip (Ref. Giovanni CAMUSSI, Giuseppe MONTRUCCHIO, Camillo ANTRO, Federico BUSSOLINO, Ciro TETTA and Giorgio EMANUELLI, "Platelet-activating Factor-mediated Contraction of Rabbit Lung Strips: Pharmacologic Modulation, Immunopharmacology 6: 87-96 (1983) has been determined using an isometric transducer connected to a Gould recorder.

The results presented in the following table showed a very significant inhibition of the PAF Acether-induced contraction.

|  | Contraction induced by PAF Acether (3 ng) (Arbitrary Units)* |
|---|---|
| Control | 39.82 ± 8.24 |
| DMSO (solvent) | 37.90 ± 6.24 |
| Ginkgolide A (30 µg/ml) | 10.30 ± 2.33 (−72.8%)** |
| Ginkgolide B (30 µg/ml) | 8.05 ± 2.16 (−78.8%)** |
| Ginkgolide C (30 µg/ml) | 11.08 ± 2.42 (−70.8%)** |

*average value of 10 determinations
**$p < 0.001$

The Ginkgolides were without significant effect on histamine-, $LTB_4$- or $LTD_4$-induced contractions.

3.2. Isolated Rat Portal Vein

In vitro experiments were performed on isolated longitudinal strips of rat portal vein maintained in Krebs-Henseleit medium at 37° C. under an oxygen-rich gaseous circulation (95% $O_2$-5% $CO_2$).

The preparations were allowed to equilibrate for 1 hour under isotonic conditions with 500 mg tension and rinced every 15 minutes. When myogenic activity was established, PAF Acether ($10^{-7}$M) is added. It induced an increase of the basal tonus and frequency of the myogenic activity.

Ginkgolide B (tested from 1 to 100 g/ml) added 30 minutes before PAF Acether exerted a dose related antagonistic effect on the increase of the basal tonus with $IC_{50} = 6.8$ µg/ml. The drug was without effect on the myogenic activity showing that it has no calcium-antagonistic activity.

3.3. Isolated Langendorff heart

The deletereous effect of PAF Acether on Isolated Langendorff heart has been previously described by J. BENVENISTE, C. BOULLET, C. BRINK and C. LABAT, Brit. J. Pharmacol, The action of PAF Acether on guinea-pig isolated heart preparation, 80: 81-3 (1983).

PAF Acether (100 pM) induced a decline in contractile strength (−30%) and a decrease of coronary flow (−50%).

Ginkgolide B ($2.10^{-4}$M) totally inhibited these phenomena. This effect was dose-dependent (disappearance of protective activity when dose $\leq 10^{-7}$M).

IV Antianaphylactic action and protective effect against fluid escape and shock

4.1. Cutaneous vascular hyperpermeability induced by PAF Acether in the rat Method: Intradermal injection of 25 ng of PAF Acether in the dorsal region of the rat with simultaneous IV injection of Evans blue dye (60 mg/kg/5 ml) induces vascular hyperpermeability and wheals formation. (for details see Basran GS, Page CP, Paul W and Morley J-Cromoglycate inhibits responses to platelet-activating factor (PAF Acether) in man: an alternative mode of action for DSCG in asthma-Eur. J. Pharma. (1983) 86 143-144).

These wheals were measured (surface in $mm^2$) at the inner side of the skin 30 mn after the injections and were taken off, put in 4 ml of formamide, incubated at 65° C. during 24 h in order to extract the dye and measure their coloration (optical density at 620 nm).

Groups of 6 Sprague-Dowley rats weighing 200 g were used and each rat received intradermal injections in two sites of the back. The experiment was performed in comparison with a reference compound, D 600 (methoxy verapamil), a calcium-blocker agent.

Treatments: Tested compounds were administered by IV route injected once simultaneously with the dye.

The results obtained are reported in the following table:

| VASCULAR HYPERPERMEABILITY INDUCED BY PAF ACETHER IN THE RAT ($p < 0.001$ for all experiments) | | | | | |
|---|---|---|---|---|---|
| | | PAF Acether induced wheal | | | |
| | Dose | Surface | | Coloration | |
| Products | mg/kg IV | $mm^2$ | % decrease | OD | % decrease |
| Control | — | 102.7 ± 4.46 | — | 1.149 ± 0.086 | — |
| D 600 (two deaths/6) | 1 | 62.6 ± 7.07 | −39 | 0.664 ± 0.099 | −42 |
| Ginkgolide A | 1 | 64.3 ± 4.2 | −37 | 0.631 ± 0.054 | −45 |
| Ginkgolide B | 1 | 58.5 ± 4.85 | −43 | 0.628 ± 0.048 | −45 |
| Ginkgolide C | 1 | 68.1 ± 6.24 | −34 | 0.701 ± 0.066 | −39 |

The Ginkgolides were without any effect on hyperpermeability induced by 5-hydroxy tryptamine 10 µg.

4.2. PAF Acether-induced shock in the rabbit

Method: Intravenous injection of PAF Acether in unanaesthetized New-Zealand rabbits weighing 2-2.5 kg induces the increase in vascular permeability leading to plasma leakage and shock: at the highest dose, some animals present bronchospasm, convulsions and die (for details see M. SANCHEZ-CRESPO, F. ALONSO, P. INARREA, V. ALVAREZ and J. EGIDO-Vascular actions of Synthetic PAF Acether in the rat: Evidence for a platelet independant mechanism Immunopharmacology 1982, 4, 173-185).

Injections of PAF Acether (3-4 nmol/kg) was performed into the ear vein (in 1 ml/kg of NaCl 0.9% containing 10 mg/ml of Blue Trypan dye).

The extravasation was quantified at time 30 mn by measuring dye concentration in the plasma (optical density at 590 nm) after blood take from the central ear artery.

Treatment: Tested compounds (Gingkolides A, B and C) or vehicle were perfused in the ear vein in 45 ml NaCl 0.9% for 1 hour before PAF Acether injection. Vehicle consisted of 1.5 ml of propylene glycol completed to 45 ml by isotonic NaCl buffer; Ginkgolides were administered at the dose of 2 mg/kg IV; the figures reported in the following table are the average values of the 10 animals of each batch.

PROTECTIVE EFFECT OF GINKGOLIDES ON PAF ACETHER-INDUCED SHOCK IN THE RABBIT

| Treatment | PAF Acether (nmol/kg) | Extravasation (O.D.) | Behaviour |
|---|---|---|---|
| Control (vehicle) | — | 0.896 | — |
| Control (PAF) | 2 | 0.991 | 1 animal died (convulsions) |
|  | 4 | 1.051 | 7 animals died (convulsions, bronchospasm) |
| Ginkgolide A | 2 | 0.903 | No death |
|  | 4 | 0.881 | No behavioural Modifications |
| Ginkgolide B | 2 | 0.827 |  |
|  | 4 | 0.880 |  |
| Ginkgolide C | 2 | 0.910 |  |
|  | 4 | 0.875 |  |

4.3. PAF Acether-induced bronchoconstriction in the anesthetized guinea-pig

Method: (For details, see B. B. VARGAFTIG, J. LEFORT, F. WAL, M. CHIGNARD and M. C. MEDEIROS-Non-steroidal anti-inflammatory drugs of combined with anti-histamine and anti-serotonin agents interfere with the bronchial and platelet effects of PAF Acether-Enr. J. Pharm. (1982) 82 121-130). Male Hartley guinea-pig (400-500 g) were anesthetized with urethane 2 g/kg Ip., tracheotomised and ventilated by mean of a respiratory pump: 70-80 strokes mn, stroke volume 5 ml, a pneumothorax was done to abolish spontaneous respiration. The right jugular vein was catherized and used for injections.

The initial resistance was kept constant at 10 cm $H_2O$ pressure according to the method of Konzett and Rössler and the overflowed airway was measured with a bronchospasm transducer UGO BASILE connected to a UGO BASILE recorder "GEMINI". Bronchial sensitivity of the animal was checked with acetylcholine (10-40 ng $kg^{-1}$ IV) and after constant response was obtained, there were injected, IV, first the propylene glycol and, five minutes later, 60 ng/kg of PAF Acether, which gave the control bronchoconstriction expressed as % of maximal bronchoconstriction given by clamping off the trachea. 40 minutes later, the tested compounds were administered by IV injection and, 5 minutes later, 60 ng/kg of PAF Acether by the same route. This experimentation was conducted on three batches of each 10 animals: first batch for Ginkgolide A, second one for Ginkgolide B and last one for Ginkgolide C, all at the 1 mg/kg dose. The figures of the following table are the average values for the 10 animals of each batch.

| Batch | % of bronchoconstriction | % of inhibition |
|---|---|---|
| Solvent | 83.6 |  |
| Ginkgolide A | 13.3 | 84.1 |
| Solvent | 80.2 |  |
| Ginkgolide B | 6.2 | 92.3 |
| Solvent | 79.4 |  |

| Batch | % of bronchoconstriction | % of inhibition |
|---|---|---|
| Ginkgolide C | 17.0 | 78.6 |

Preliminary clinical trials in shock

An open study has been performed on 13 thermal-injured patients (total burnt surface area >50%) treated by Ginkgolide B.

It has been recently shown that leukotriene and PAF Acether seem to be involved in fluid escape, oedema and anergy which characterize the thermal injury (BRAQUET Monique et al., Lancet, in Press; Comptes-rendus de l'Académie des Sciences, in Press).

The Ginkgolide B was administered in a perfusion (5 mg per hour for six hours and then 2 mg per hour for the following 48 hours). It has been noticed that this treatment leads to a faster recovery (decreased oedema, decreased plasma leakage and improvement of clinical outcome).

TOXICITY

The $LD_{50}$ was not reached at the dose of 600 mg/kg per os on mice and rats: these compounds have a very low toxicity especially if this value is compared to the doses to be used.

PRESENTATION-POSOLOGY

For human use, these compounds may be presented in tablets and gelatine capsules for oral use, in phials for IV administration or in spray for inhalation. The following figures indicate daily doses.

(a) Oral route:

In human therapy, when using the most active of these compounds, Ginkgolide B, oral doses are from 10 to 150 mg; if Ginkgolides A or C are used, corresponding doses are from 20 to 250 mg and if Ginkgolide M is used, from 50 to 300 mg.

Preferred form for oral use comprises gelatine capsules containing 20 mg of Ginkgolide B or corresponding doses of the other Ginkgolides.

(b) IV route:

In human therapy, when using the most active of these compounds, Ginkgolide B, IV route doses are comprised between 1 and 20 mg; if Ginkgolides A or C are used, corresponding doses are from 2 to 50 mg, and if Ginkgolide M is used, from 5 to 70 mg.

The preferred dosage when Ginkgolide B is used are phials of 2 ml of isotonic solution containing 2 mg of said Ginkgolide (corresponding doses of Ginkgolides A, C or M may be substituted to the 2 mg of Ginkgolide B).

(c) Spray route:

In human therapy, when using the most active of these compounds, Ginkgolide B, the spray-canister for 200 sprays may contain 200 mg of Ginkgolide associated with the appropriate propulsing gas; if Ginkgolides A or C are used, the spray-canister should contain 250 mg of Ginkgolide and if Ginkgolide M is used, it should contain 400 mg.

What is claimed is:

1. A pharmaceutical composition comprising a pharmaceutically acceptable carrier and a ginkgolide or a pharmaceutically acceptable derivative thereof, the ginkgolide being present in an amount effective to treat a PAF Acether-induced malady.

2. The pharmaceutical composition of claim 1 wherein the ginkgolide is selected from the group consisting of Ginkgolide A, Ginkgolide B, Ginkgolide C and Ginkgolide M.

3. The pharmaceutical composition of claim 1 wherein the ginkgolide is Ginkgolide B, the composition is adapted for oral administration, and the Ginkgolide B is present in the amount of from 10–150 mg.

4. The pharmaceutical composition of claim 1 wherein the ginkgolide is Ginkgolide B, the composition is adapted for intravenous administration, and the Ginkgolide B is present in the amount of from 1–20 mg.

5. The pharmaceutical composition of claim 1 wherein the ginkgolide is Ginkgolide B, the composition is adapted for spray inhalation, and the Ginkgolide B is present in an amount of about 1 mg. per spray dose.

6. A method of treating or preventing a PAF Acether-induced malady in a human or animal in need of such treatment comprising the administration in a pharmaceutically acceptable carrier of 1 to 50 mg/kg of a ginkgolide or a pharmaceutically acceptable derivative thereof to treat the PAF Acether-induced malady.

7. A method of treating or preventing a PAF Acether-induced malady in a human in need of such treatment comprising the administration in a pharmaceutically acceptable carrier of 1 to 50 mg/kg of a ginkgolide selected from the group consisting of Ginkgolide A, Ginkgolide B, Ginkgolide C, and Ginkgolide M, or a pharmaceutically acceptable derivative thereof, to treat the PAF Acether-induced malady.

8. A method of treating or preventing a PAF Acether-induced malady in a human in need of such treatment comprising the administration in a pharmaceutically acceptable carrier of 1 to 50 mg/kg of a ginkgolide selected from the group consisting of Ginkgolide A, Ginkgolide B, and Ginkgolide C, or a pharmaceutically acceptable derivative thereof, to treat the PAF Acether-induced malady.

9. A method of treating or preventing a PAF Acether-induced malady in a human in need of such treatment comprising the administration in a pharmaceutically acceptable carrier of 1 to 50 mg/kg of Ginkgolide B, or a pharmaceutically acceptable derivative thereof, to treat the PAF Acether-induced malady.

10. A method of treating or preventing a PAF Acether-induced malady in an animal in need of such treatment comprising the administration in a pharmaceutically acceptable carrier of 1 to 50 mg/kg of a ginkgolide selected from the group consisting of Ginkgolide A, Ginkgolide B, Ginkgolide C, and Ginkgolide M, or a pharmaceutically acceptable derivative thereof, to treat the PAF Acether-induced malady.

11. A method of treating or preventing a PAF Acether-induced malady in an animal in need of such treatment comprising the administration in a pharmaceutically acceptable carrier of 1 to 50 mg/kg of a ginkgolide selected from the group consisting of Ginkgolide A, Ginkgolide B, and Ginkgolide C, or a pharmaceutically acceptable derivative thereof, to treat the PAF Acether-induced malady.

12. A method of treating or preventing a PAF Acether-induced malady in an animal in need of such treatment comprising the administration in a pharmaceutically acceptable carrier of 1 to 50 mg/kg of Ginkgolide B, or a pharmaceutically acceptable derivative thereof, to treat the PAF Acether-induced malady.

* * * * *

UNITED STATES PATENT AND TRADEMARK OFFICE
CERTIFICATE OF CORRECTION

PATENT NO. : 4,734,280

DATED : March 29, 1988

INVENTOR(S) : Pierre Braquet

It is certified that error appears in the above-identified patent and that said Letters Patent are hereby corrected as shown below:

Column 1, line 56, change "KOHI" to --KOJI--.

At the top of Column 3, insert the following paragraph:

--Ginkgolides A and B are powerful inhibitors of PAF Acether-induced PA, more potent than the reference compound kadsurenone and ginkgolides C and M.--

Signed and Sealed this

Fifteenth Day of November, 1988

Attest:

DONALD J. QUIGG

Attesting Officer

Commissioner of Patents and Trademarks